US 9,759,793 B2

(12) United States Patent
Kim et al.

(10) Patent No.: US 9,759,793 B2
(45) Date of Patent: Sep. 12, 2017

(54) OBJECT DISCRIMINATION METHOD USING ULTRA-LOW MAGNETIC FIELD NUCLEAR MAGNETIC RESONANCE AND AN OBJECT DISCRIMINATION APPARATUS OF THE SAME

(71) Applicant: Korea Research Institute of Standards and Science, Daejeon (KR)

(72) Inventors: Kiwoong Kim, Daejeon (KR);
Chan-Seok Kang, Daejeon (KR);
Seong-Joo Lee, Daejeon (KR);
Yong-ho Lee, Daejeon (KR);
Kwon-Kyu Yu, Daejeon (KR)

(73) Assignee: KOREA RESEARCH INSTITUTE OF STANDARDS AND SCIENCE, Daejeon (KR)

(*) Notice: Subject to any disclaimer, the term of this patent is extended or adjusted under 35 U.S.C. 154(b) by 707 days.

(21) Appl. No.: 14/262,251

(22) Filed: Apr. 25, 2014

(65) Prior Publication Data

US 2014/0232400 A1  Aug. 21, 2014

Related U.S. Application Data

(63) Continuation of application No. PCT/KR2012/008426, filed on Oct. 16, 2012.

(30) Foreign Application Priority Data

Oct. 26, 2011  (KR) .......................... 10-2011-0109971

(51) Int. Cl.
*G01V 3/00* (2006.01)
*G01R 33/44* (2006.01)
(Continued)

(52) U.S. Cl.
CPC .......... *G01R 33/448* (2013.01); *G01N 24/08* (2013.01); *G01R 33/445* (2013.01); *G01R 33/326* (2013.01)

(58) Field of Classification Search
CPC .. G01R 33/448; G01R 33/445; G01R 33/326; G01N 24/08
(Continued)

(56) References Cited

U.S. PATENT DOCUMENTS 7,688,069 B2 * 3/2010 Kraus .................. G01R 33/445
  324/309
8,350,568 B2 1/2013 Hwang et al.
(Continued)

FOREIGN PATENT DOCUMENTS

CN    1643403 A    7/2005
CN  101975788 A    2/2011
(Continued)

OTHER PUBLICATIONS

International Search Report for Application No. PCT/KR2012/008426 dated Mar. 8, 2013.
(Continued)

*Primary Examiner* — Susan Lee
(74) *Attorney, Agent, or Firm* — Jenkins, Wilson, Taylor & Hunt P.A.

(57) ABSTRACT

Provided are an object discrimination method and an object discrimination apparatus using an ultra-low magnetic field nuclear magnetic resonance (NMR). The method includes measuring the respective spin-lattice relaxation times at a plurality of strengths of prepolarization magnetic fields with respect to a measurement target and classifying the measurement target using the spin-lattice relaxation times.

5 Claims, 14 Drawing Sheets

(51) Int. Cl.
*G01N 24/08* (2006.01)
*G01R 33/32* (2006.01)

(58) Field of Classification Search
USPC .......................................................... 324/309
See application file for complete search history.

(56) References Cited

U.S. PATENT DOCUMENTS

| | | | |
|---|---|---|---|
| 2010/0219827 A1 | 9/2010 | Matlashov et al. | |
| 2011/0068789 A1* | 3/2011 | Hwang | G01R 33/445 324/307 |
| 2012/0001631 A1* | 1/2012 | Espy | G01R 33/448 324/309 |

FOREIGN PATENT DOCUMENTS

| | | |
|---|---|---|
| JP | H 07-198636 A | 8/1995 |
| JP | H 10-142175 A | 5/1998 |
| JP | 2002/090321 | 3/2002 |
| JP | 2008-229048 A | 10/2008 |
| KR | 10-2011-0031723 A | 3/2011 |
| WO | WO 9859220 A2 | 12/1998 |

OTHER PUBLICATIONS

Chinese Office Action for Application No. 201280052725.4 dated Sep. 25, 2015.
B.P. Hills, Application of Low-field NMR to Food Science, Annual Reports on NMR Spectroscopy, 2006, 177page-230page, vol. 58, Academic Press.
Shan-Shan Chen/ Ran Li/ Jie Yu/ Hong-Zhi Wang/ Xue-Long Zhang, The principle and application of nuclear magnetic resonance analyst instrument in lowfield ((永磁低场 核磁共振 分析仪原 理和应用), Life Science Instruments(生命科学仪器), 2009, 49page-53page, Issue 10, Life Science Instruments editorial department.

* cited by examiner

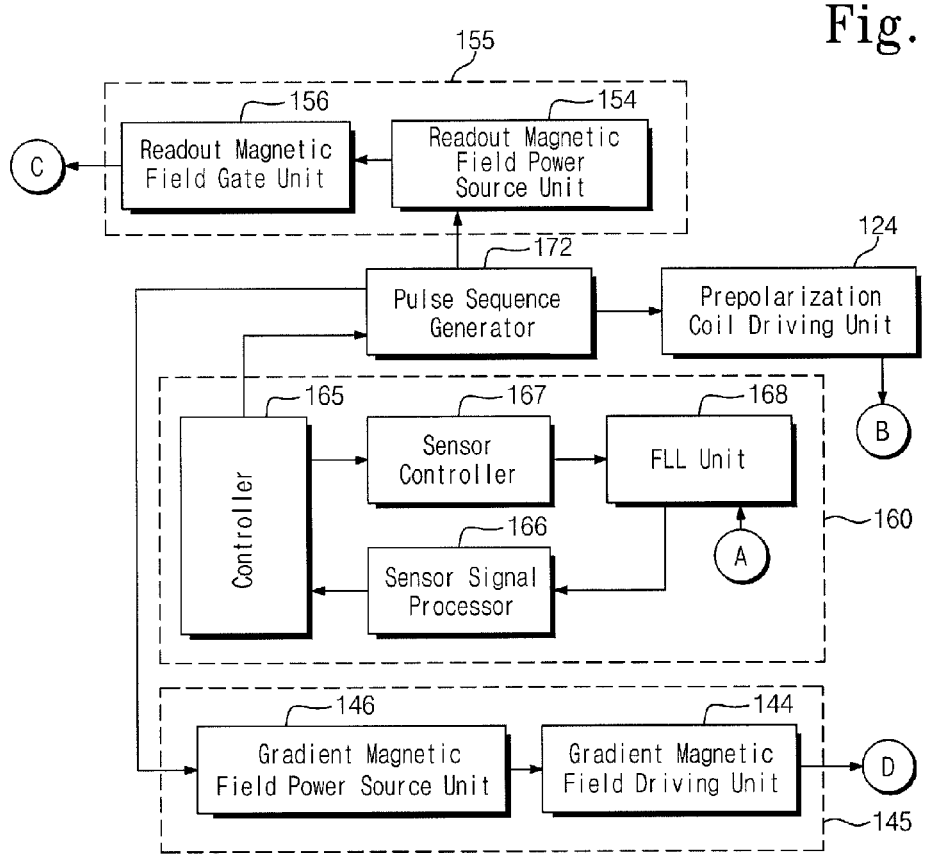
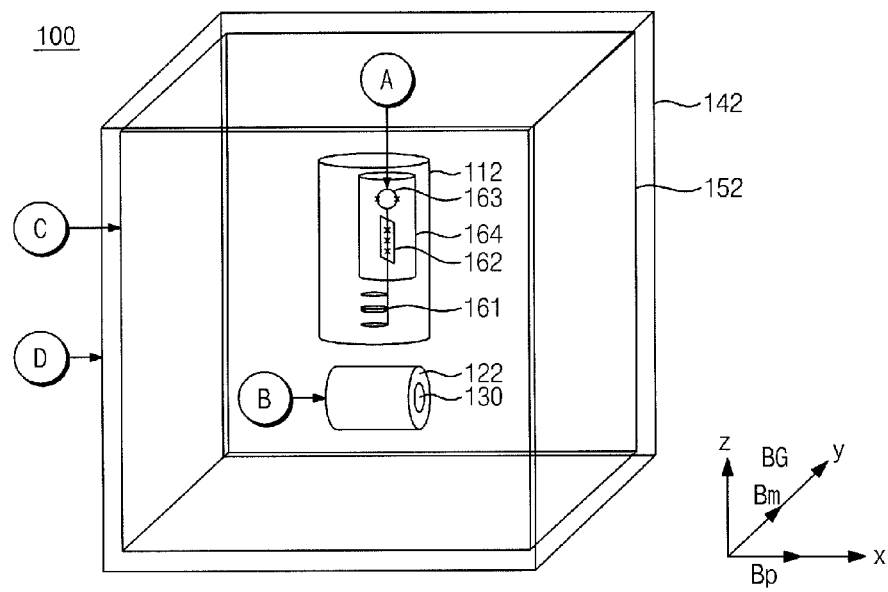
Fig. 1

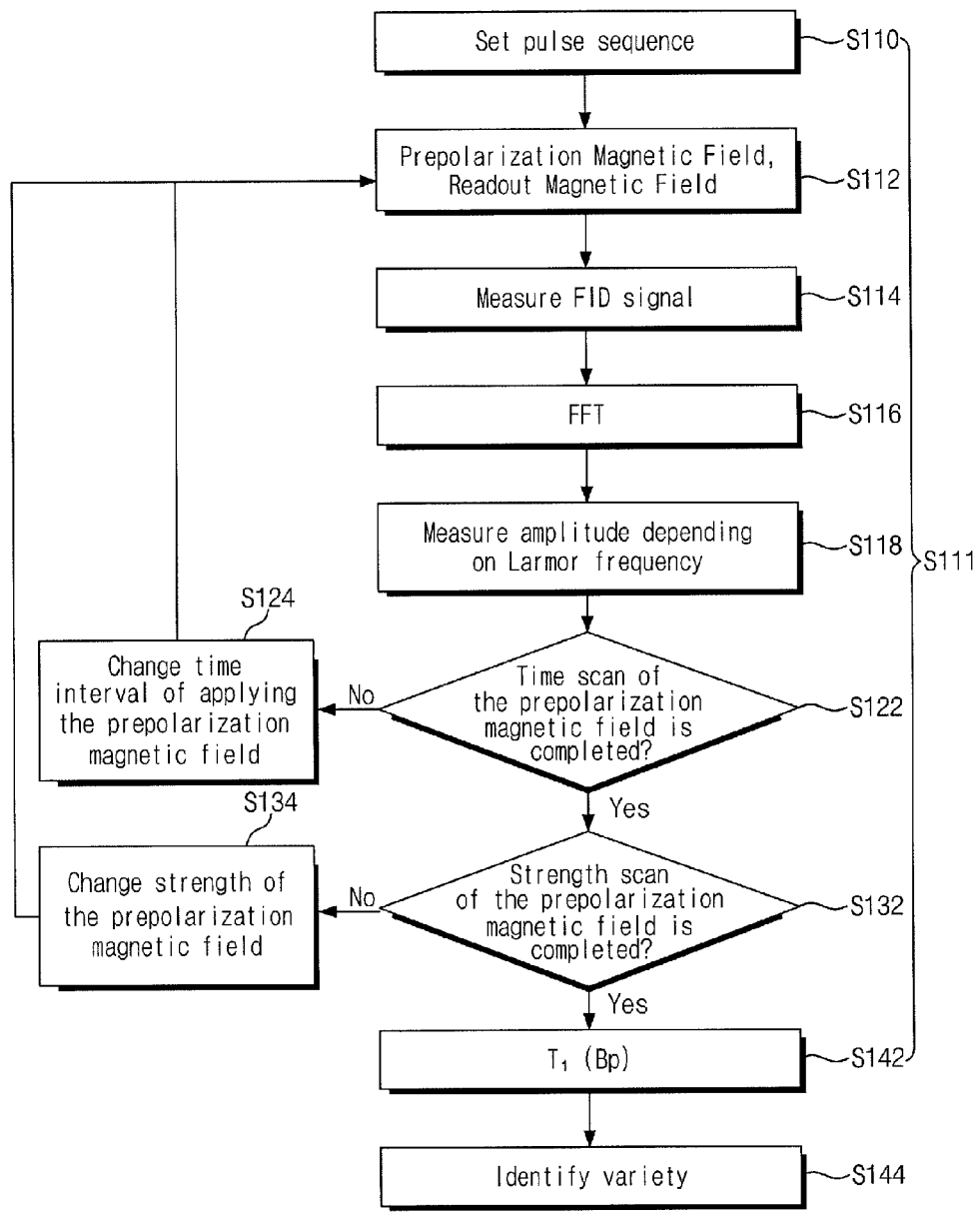

OBJECT DISCRIMINATION METHOD USING ULTRA-LOW MAGNETIC FIELD NUCLEAR MAGNETIC RESONANCE AND AN OBJECT DISCRIMINATION APPARATUS OF THE SAME

CROSS-REFERENCE TO RELATED APPLICATIONS

This application is a continuation of and claims priority to PCT/KR2012/008426 filed on Oct. 16, 2012, which claims priority to Korea Patent Application No. 10-2011-0109971 filed on Oct. 26, 2011, the entirety of which is incorporated by reference herein.

BACKGROUND

Field of the Invention

The present invention described herein generally ultra-low magnetic field object discrimination methods, more particularly, an ultra-low magnetic field object discrimination method for discriminating measurement targets using a measured spin-lattice relaxation time while varying a prepolarization magnetic field or a readout magnetic field with an unsaturated spin-lattice relaxation time.

Background Art

Nuclear magnetic resonance (hereinafter referred to as "NMR") is a phenomenon that a magnetic spin of the nuclei of atoms precesses in resonance with the magnetic field when a magnetic field is applied to nuclei of atoms constituting all substances. A main magnet of a conventional NMR must spatially uniformly generate a magnetic field of 0.1 Tesla to several Teslas. Therefore, a superconducting main magnet generating the magnetic field is large in volume and high in cost.

Low magnetic field/ultra-low magnetic NMR divides a magnetic field generated by the main magnet of the conventional NMR into a prepolarization magnetic field and a readout magnetic field. Thus, the strength of the readout magnetic field may decrease as tens of microTeslas or several microTeslas.

Low magnetic field/ultra-low magnetic field NMR includes a prepolarization coil generating the prepolarization magnetic field and a readout coil generating the readout magnetic field. The prepolarization coil generates a prepolarization magnetic field to prepolarize a measurement target object. Afterwards, the prepolarization magnetic field is eliminated and the readout magnetic field is applied to the target object, and then a detector measures a nuclear magnetic resonance signal that emerges while the magnetization of the target object is relaxed. Thus, the prepolarization coil has only to generate a strong magnetic field although the uniformity of the prepolarization magnetic field is reduced. In addition, the readout coil has only to generate a uniform but weak readout magnetic field. Therefore, low magnetic field/ultra-low magnetic field NMR may be simple in structure and low in cost. As the strength of the readout magnetic field decreases, a readout signal frequency corresponding to a Larmor frequency in proportion to the strength of a magnetic field decreases as several kilohertz (kHz) or hundreds of Hertz (Hz).

Therefore, it is possible to measure a phenomenon that does not occur in conventional high magnetic field NMR. In the low magnetic field/ultra-low magnetic field NMR, distortion caused by a metal is significantly low. As a result, a material inside a metal can or a packaged material may be non-destructively measured.

SUMMARY

Some embodiments of the present invention provide an object discrimination method using an ultra-low magnetic field nuclear magnetic resonance (NMR).

Some embodiments of the present invention provide an object discrimination apparatus using an ultra-low magnetic field nuclear magnetic resonance (NMR).

An object discrimination method using an ultra-low magnetic field nuclear magnetic resonance (NMR) according to an embodiment of the present invention may include measuring the respective spin-lattice relaxation times at a plurality of strengths of prepolarization magnetic fields with respect to a measurement target; and classifying the measurement target using the spin-lattice relaxation times.

In an embodiment of the present invention, measuring the respective spin-lattice relaxation times may include setting a pulse sequence suitable for individual relaxation time characteristics of the measurement target; applying a prepolarization magnetic field and a readout magnetic field; measuring a free induction decay (FID) signal; measuring the signal intensity or line width of the resonance frequency of a nucleus by Fourier-transform of the FID signal; changing the time interval of applying the prepolarization magnetic field; obtaining the spin-lattice relaxation time by fitting the signal intensity variation depending on the time interval of applying the prepolarization magnetic field; and constructing the first parameter vector with obtaining the respective spin-lattice relaxation times by repeatedly performing the above operations on a plurality of changed strengths of prepolarization magnetic fields. The variety of the measurement target is identified using the first parameter vector.

In an embodiment of the present invention, the method may further include measuring the spin-spin lattice time $T_2$ of the measurement target using a gradient echo signal; and classifying the measurement target using the spin-spin relaxation time.

In an embodiment of the present invention, measuring the spin-spin relaxation time of the measurement target may include setting a pulse sequence suitable for individual relaxation time characteristics of the measurement target; applying a prepolarization magnetic field and a readout magnetic field; successively applying a positive gradient magnetic field and a negative gradient magnetic field; measuring a gradient echo signal; measuring the signal line width of the resonance frequency of a nucleus by Fourier-transform of the gradient echo signal; and constructing the second parameter vector with a line width or a reciprocal of the line width depending on the resonance frequency of a nucleus. The variety of the measurement target is identified using the second parameter vector.

An object discrimination method using an ultra-low magnetic field nuclear magnetic resonance (NMR) according to another embodiment of the present invention may include measuring the signal line width of the resonance frequency of a nucleus by Fourier-transforming the measured free induction decay (FID) signal while changing the strength of a readout magnetic field to a measurement target; and classifying the measurement target using the signal line width of the resonance frequency of a nucleus.

In an embodiment of the present invention, measuring the signal line width may include setting a pulse sequence suitable for individual relaxation time characteristics of the measurement target; applying a prepolarization magnetic field; applying the readout magnetic field; measuring a free induction decay (FID) signal; measuring the signal line width of the resonance frequency of a nucleus by Fourier-transform of the FID signal; changing the strength of the readout magnetic field; and constructing the third parameter vector with the signal line width of the resonance frequency of a nucleus depending on the strength of the readout magnetic field by repeatedly measuring the above operations. The variety of the measurement target is identified using the third parameter vector.

An object discrimination method using an ultra-low magnetic field nuclear magnetic resonance (NMR) according to another embodiment of the present invention may include constructing the first parameter vector with obtaining the respective spin-lattice relaxation times with respect to a plurality of strengths of prepolarization magnetic fields; constructing the second parameter vector with a line width or a reciprocal of the line width depending on the resonance frequency of a nucleus by using a gradient echo signal; constructing the third parameter vector with values of the signal line width of the resonance frequency of a nucleus depending on the strength of a readout magnetic field; constructing a new parameter vector with combining components of the first to third parameter vectors; and identifying the variety of a measurement target using the new parameter vector.

An object discrimination method using an ultra-low magnetic field nuclear magnetic resonance (NMR) according to another embodiment of the present invention may include constructing the first parameter vector with obtaining the respective spin-lattice relaxation time with respect to a plurality of strengths of prepolarization magnetic fields; constructing the second parameter vector with a line width or a reciprocal of the line width depending on the resonance frequency of a nucleus by using a gradient echo signal; constructing the third parameter vector with values of the signal line width of the resonance frequency of a nucleus depending on the strength of a readout magnetic field; constructing a new parameter vector with combining components of the first to third parameter vectors; collecting new parameter vectors for respective materials from repeating measurement for various materials desired to be discriminated; reducing a parameter vector dimension by finding out an effective principal vector component for classification with applying support vector machine (SVM) or principal component analysis (PCA) to the collected new parameter vectors and projecting the new parameter vector into the principal vector component; and identifying the variety of the material using the component of the reduced parameter vector dimension.

An object discrimination apparatus using an ultra-low magnetic field nuclear magnetic resonance (NMR) according to an embodiment of the present invention may include a Dewar containing a low-temperature liquid refrigerant; a prepolarization coil prepolarizing a measurement target; a prepolarization coil driver generating a prepolarization magnetic field Bp by intermittently applying current to the prepolarization coil; a sensor unit measuring a nuclear magnetic resonance (NMR) signal of the measurement target to which the prepolarization magnetic field Bp is applied by the prepolarization coil; a readout coil applying a readout magnetic field to the measurement target; and a readout magnetic field power source unit applying the readout magnetic field to the measurement target by applying current to the readout coil, and wherein the sensor unit measures the respective spin-lattice relaxation times $T_1$ of the measurement target at a plurality of strengths of prepolarization magnetic fields and classifies the measurement target using the spin-lattice relaxation times $T_1$.

In an embodiment of the present invention, the apparatus may further include a gradient magnetic field coil applying a gradient magnetic field to the measurement target; a gradient magnetic field driving unit supplying current to the gradient magnetic field coil; a gradient magnetic field power source unit supplying a power source to the gradient magnetic field driving unit; and a pulse sequence generator providing a pulse sequence to the prepolarization magnetic field driving unit, the readout magnetic field power source unit, and the gradient magnetic field power source unit.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present invention.

FIG. 1 illustrates an ultra-low magnetic field NMR apparatus for variety discrimination according to an embodiment of the present invention.

FIG. 2 is a flowchart illustrating an object discrimination method using the ultra-low magnetic field NMR device in FIG. 1.

DETAILED DESCRIPTION

Figure 3A:
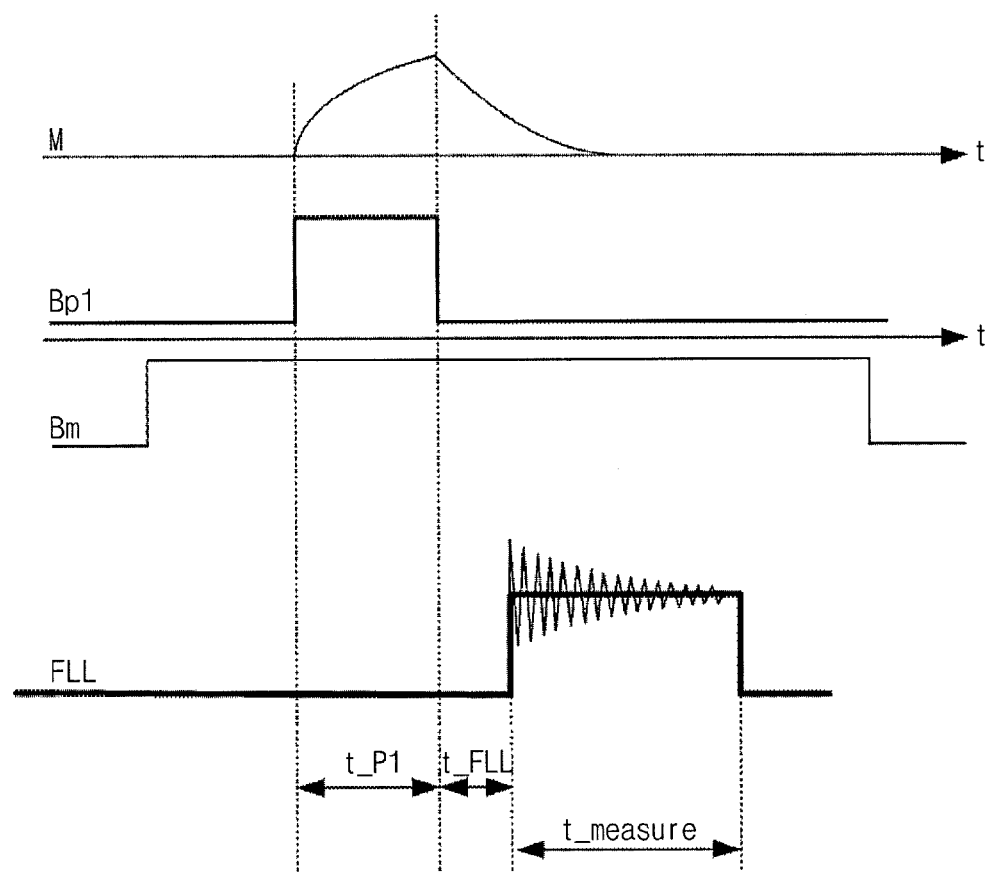
FIGS. 3A and 3B illustrate a pulse sequence according to an embodiment of the present invention.

In a conventional high magnetic field NMR/MRI, an MR signal is a signal generated by a hydrogen nucleus and an image is displayed depending on an H nucleus concentration of water molecules in a human body. Therefore, a magnetic resonance image indicates a spatial concentration of the hydrogen nucleus. In the high magnetic field NMR/MRI, $T_1$ is a spin-lattice relaxation time and $T_2$ is a spin-spin relaxation time. A living tissue may have different $T_1$ and/or $T_2$ under a fixed main magnetic field. Magnetic resonance imaging (MRI) is a spatial distribution of spatial $T_1$ or $T_2$. However, since the high magnetic field NMR/MRI has difficulty in changing the strength of a main magnetic field, it is difficult to find out varieties of agricultural and livestock products.

In ultra-low magnetic field NMR, a spin-lattice relaxation time $T_1$ may be a function of a prepolarization magnetic field Bp and/or a readout magnetic field Bm. The prepolarization magnetic field Bp and/or the readout magnetic field Bm may be easily changed in the ultra-low magnetic field NMR. Therefore, the measured $T_1$ according to the prepolarization magnetic field Bp, the measured line width of an FID signal according to the readout magnetic field Bm, or the $T_2$ obtained by processing a gradient echo signal may be used to discriminate a measurement target.

For example, a specific living tissue of one variety may have different $T_1$ dependency with that of another variety. The measured $T_1$ dependency may be used to discriminate varieties of measurement targets that cannot be identified by the naked eye. The measurement targets may be, for example, fruits, vegetables, alcoholic drinks, fishes, and meats.

Korean native cattle and U.S. cattle are different in variety and may be presently discriminated only by a DNA test. However, the DNA test requires a lot of time and destruction of a measurement target. Accordingly, there is a need for a novel method for discriminating varieties of livestock. Thus, ultra-low NMR may be used to discriminate varieties of livestock.

According to an embodiment of the present invention, the $T_1$ may be measured under different conditions to discriminate variety of a measurement target.

The present invention will now be described more fully hereinafter with reference to the accompanying drawings, in which preferred embodiments of the present invention are shown. However, the present invention may be embodied in many different forms and should not be construed as limited to the embodiments set forth herein. Rather, these embodiments are provided so that this disclosure will be thorough and complete, and will fully convey the scope of the present invention to those skilled in the art. Like numbers refer to like elements throughout.

FIG. 1 illustrates an ultra-low magnetic field NMR apparatus for variety discrimination according to an embodiment of the present invention.

Referring to FIG. 1, an object discrimination apparatus 100 using an ultra-low magnetic field NMR includes a Dewar 112 containing a low-temperature liquid refrigerant, a prepolarization coil 122 prepolarizing a measurement target 130, a prepolarization coil driver 124 generating a prepolarization magnetic field Bp by intermittently applying current to the prepolarization coil 122, a sensor unit 160 measuring a nuclear magnetic resonance (NMR) signal of the measurement target 130 to which the prepolarization magnetic field Bp is applied by the prepolarization coil 122, a readout coil 152 applying a readout magnetic field Bm to the measurement target 130, and a readout magnetic field power source unit 154 applying the readout magnetic field Bm to the measurement target 130 by applying current to the readout coil 152.

The sensor unit 160 discriminates the variety of the measurement target 130 using the spin-lattice relaxation time $T_1$ extracted by the processing of an obtained NMR signal while changing the strength or the time interval of the prepolarization magnetic field Bp applied to the measurement target 130.

The sensor unit 160 measures the respective spin-lattice relaxation times $T_1$ of the measurement target 130 at a plurality of strengths of prepolarization magnetic fields and classifies the measurement target 130 using the spin-lattice relaxation times T1.

A gradient magnetic field coil 142 may apply a gradient magnetic field BG to the measurement target 130. A gradient magnetic field driver 144 supplies current to the gradient magnetic field coil 142 to apply the gradient magnetic field BG to the measurement target 130. A gradient magnetic field power source unit may supply a power source to the gradient magnetic field driver 144. The gradient magnetic field power source unit 146 supplies the power to the gradient magnetic field driver 144 by receiving a pulse sequence from a pulse sequence generator 172.

The pulse sequence generator 172 provides a pulse sequence to the prepolarization coil driver 124, the readout magnetic field power source unit 154, and the gradient magnetic field power source unit 146 by receiving a control signal from a controller 165.

The sensor unit 160 may include a magnetic flux transformer 161 sensing and/or attenuating/amplifying a magnetic flux, a superconducting quantum interference device (SQUID) 163 receiving an output signal of the magnetic flux transformer 161 and detecting a magnetic field to convert the output signal as a voltage signal, a flux locked loop (FLL) unit 168 linearizing the voltage signal and providing the linearized voltage signal that is proportional to a detected magnetic field, a sensor signal processor 166 processing the linearized voltage signal to remove the noise and amplifying the processed voltage signal, and a sensor controller 167 providing a control signal to the FLL unit 168.

The SQUID 163 is a type of transducer for converting the variation of an external magnetic flux to a voltage signal by combination of the Josephson effect and the magnetic flux quantization effect that only superconductors exhibit. The SQUID 163 is a magnetic sensor that consists of one or two Josephson junctions inserted into a single superconducting loop. An RF SQUID is a magnetic sensor that consists of one Josephson junction inserted into a single superconducting loop. A DC SQUID is a magnetic sensor that consists of two Josephson loops inserted into a single superconducting loop. The RF SQUID operates in the manner that an AC voltage of RF frequency band is output and its frequency varies depending on an applied magnetic flux. The DC SQUID operates in the manner that a DC voltage is generated as a function of an applied magnetic flux. The function is given in the form of a function vibrating in cycles of $\Phi_0(=2.07 \times 10^{\wedge}(-15)\text{Wb})$ that is a quantum value of the magnetic flux. The detailed form of the flux/voltage conversion function may be decided depending on detailed structures of the DC SQUID.

The magnetic flux transformer 161 may include a pick-up coil sensing a magnetic flux and converting the magnetic flux to the superconducting current and/or an input coil transferring the converted magnetic flux to the SQUID 163 after amplifying or attenuating the magnetic flux converted from the superconducting current. The magnetic flux transformer 161 may be formed of a superconductor. The pick-up coil may have a large area to sense many magnetic fluxes. The input coil may have a similar area to that of the SQUID 163 to focus the magnetic fluxes to the SQUID 163 and may be wound many times to change its amplification or attenuation rate. The magnetic flux transformer 161 may include a magnetometer where a pick-up coil consists of one loop or a gradiometer where a pick-up coil consists of one or more pairs of loops wound in opposite directions.

The SQUID 163 may be connected to the FLL unit 168 through a conductor. The SQUID 163 need to be protected such that the SQUID 163 may stably operate under a very large magnetic field such as a prepolarization magnetic field Bp. Therefore, an ultra-low magnetic field-MRI system uses a superconducting shield 164 to protect a SQUID. However, the SQUID cannot function as a magnetic field sensor when the overall SQUID sensor is superconductively shielded. For this reason, when shielding is performed using a superconductor, only a SQUID portion and an input coil portion of a magnetic flux transformer are superconductively shielded and a readout coil is located outside the superconducting shield. In this case, the SQUID itself is protected from a strong magnetic field due to the superconducting shield 164 but current inducted from the readout coil cannot be prevented from applying to the SQUID. Thus, a current restriction unit 162 is disposed in the ultra-low magnetic field-NMR system to prevent the overcurrent induced from the readout coil from applying to the SQUID.

The FLL unit 168 may include an input terminal to receive an output signal of the SQUID 163, an integrator, a feedback linearization circuit, a feedback coil, and the like. The FLL unit 168 may output a magnetic flux variation amount after converting the magnetic flux variation amount to a voltage signal having a much wider range than a flux quantum value $\Phi_0$.

A readout magnetic field generator 155 may generate a readout magnetic field Bm that is spatially uniform and weak. The readout magnetic field generator 155 may include a readout magnetic field power source unit 154, a readout magnetic field gate unit 156, and a readout coil 152. The readout magnetic field gate unit 156 may adjust current applied to the readout coil 152 to intermittently generate the readout magnetic field Bm.

A gradient magnetic field generator 145 may include a gradient magnetic field power source unit 146, a gradient magnetic field driver 144, and a gradient magnetic field coil 142 to generate a y-component of the gradient magnetic field dBy/dy.

The pulse sequence generator 172 may generate a pulse sequence and provide the pulse sequence to the prepolarization coil driver 124, the readout magnetic field power source unit 154, and the gradient magnetic field power source unit 146 to obtain the T1, T2, and line widths of FID signals.

The controller 165 may process a signal of the sensor signal processor 166 and control the pulse sequence generator 172 and the sensor controller 167.

An optical sold state relay (SSR) may be used as a switch to turn on/off the prepolarization magnetic field Bp, the readout magnetic field Bm, and the gradient magnetic field BG. While the SSR is turned off, the prepolarization coil 122, the readout coil 152, and the gradient magnetic field coil 142 are completely short-circuited from a current source. A TTL signal for driving the SSR may be applied through the optical communication. Thus, all electrical connections having an adverse effect on the sensor unit 160 may be removed.

The prepolarization coil 122 may generate a prepolarization magnetic field Bp for prepolarizing the measurement target 130. The prepolarization coil 122 may be in the form of a solenoid where a copper line having a diameter of 1 millimeter (mm) is wound total 240 times onto a bore having an external diameter of 30 mm and a length of 60 mm. The total resistance of the prepolarization coil 122 is 0.75 ohm and an inductance thereof is 0.79 mH at 1 kHz.

A 12 V Pb battery may be used as a current source to minimize a noise having an effect on the sensor unit 160. A magnetic field in the internal center of the prepolarization coil 122 measured by using a gaussmeter having a resolution of 0.01 mT may be about 50 mT.

The readout coil 152 may apply the readout magnetic field Bm to the measurement target. The readout coil may be a Helmholtz-type square coil whose one side has a length of 1340 mm. A magnetic field in the center of the readout coil measured by using a fluxgate is about 2.82 Gauss. A Larmor frequency of the hydrogen nucleus corresponding to the magnetic field having this strength is about 120 Hz.

A Larmor frequency of the hydrogen, carbon or nitrogen nucleus may vary depending on the strength of the readout magnetic field. Accordingly, a Larmor frequency of the hydrogen, carbon or nitrogen nucleus in a predetermined readout magnetic field may be fixed. When a free induction decay (FID) signal is Fourier-transformed, the amplitude at a Larmor frequency varies depending on the time interval of the fixed strength of the prepolarization magnetic field or the strength of the prepolarization magnetic field. Thus, the $T_1$ may be obtained.

The gradient magnetic field coil 142 may apply a gradient magnetic field. The gradient magnetic field coil 142 may be a Maxwell pair type in which magnetic fields having opposite polarities are applied to two coils facing each other. One side of the gradient magnetic field coil 142 has a length of 1420 mm, and a magnetic field gradient in the center of the gradient magnetic field coil 142 measured using a fluxgate is about 31.3 pT/cm. The gradient of the magnetic field dBy/dy is equivalent to about 1.33 Hz/cm as expressed with a frequency component.

FIG. 2 is a flowchart illustrating an object discrimination method using the ultra-low magnetic field NMR device in FIG. 1.

Figure 3B:
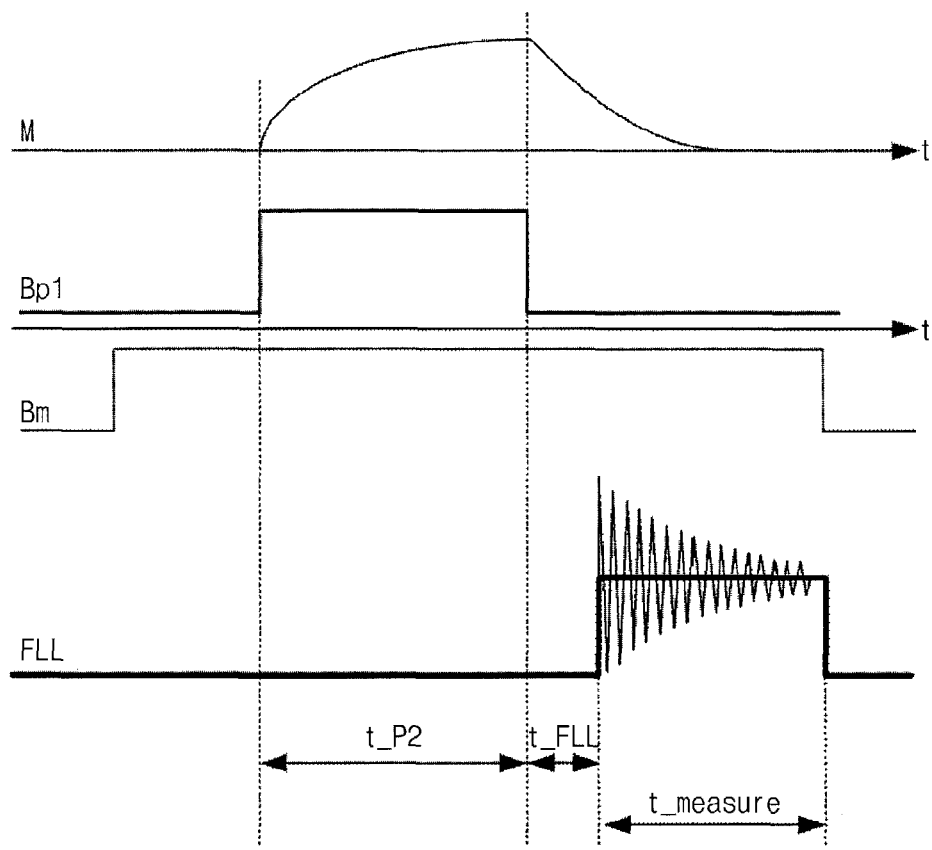

FIGS. 3A and 3B illustrate a pulse sequence according to an embodiment of the present invention.

Referring to FIGS. 2, 3A, and 3B, an object discrimination method using an ultra-low magnetic field NMR object includes measuring the respective spin-lattice relaxation times $T_1$ at a plurality of strengths of prepolarization magnetic fields with respect to a measurement target (S111) and classifying the measurement target using the spin-lattice relaxation time $T_1$ (S144).

The measurement target is mounted on an ultra-low magnetic field NMR device. A pulse sequence of the ultra-low magnetic field NMR device is decided. A pulse sequence to measure the $T_1$ may have two types of ways.

One ways is to measure a free induction decay (FID) signal while changing the time interval of applying the prepolarization magnetic field at the fixed strength of the prepolarization magnetic field. Accordingly, the degree of the polarization of a measurement target is decided depending on the time interval of applying the prepolarization magnetic field. The measured FID signal may be Fourier-transformed (S116). Thereafter, the amplitude is obtained by Fourier transformation based on the frequency. The amplitude is obtained at a resonance frequency of the hydrogen nucleus (S118).

The amplitude at the resonance frequency of the hydrogen nucleus may be measured depending on the time interval of applying the prepolarization magnetic field (S124). The amplitude at the resonance frequency of the hydrogen nucleus depending on the time interval of applying the prepolarization magnetic field is saturated as the time interval increases. The amplitude may have an exponential functional dependency with respect to the time interval, and the $T_1$ may be obtained by fitting an exponential function (S142).

The operation S111 includes setting a pulse sequence suitable for an individual relaxation time characteristic of the measurement target (S110), applying the prepolarization magnetic field and a readout magnetic field (S112), measuring a free induction decay (FID) signal (S114), measuring the signal intensity or line width of the resonance frequency of a nucleus by Fourier-transform of the FID signal (S118), changing the time interval of applying the prepolarization magnetic field (S124), obtaining the $T_1$ by fitting the change of the signal intensity depending on the time interval of applying the prepolarization magnetic field (S142), and constructing the first parameter vector with obtaining the respective spin-lattice relaxation times $T_1$ by repeatedly performing the above operations on a plurality of changed strengths of prepolarization magnetic fields (S134). The variety of the measurement target is discriminated using the first parameter vector.

Referring to FIG. 3A, a pulse sequence to measure the $T_1$ may apply a prepolarization magnetic field Bp1 and a readout magnetic field Bm sequentially or simultaneously. The readout magnetic field Bm is preferably applied when the prepolarization magnetic field Bp1 is turned off. The strength of the prepolarization magnetic field Bp1 is constant. The time interval t_P1 of applying the prepolarization magnetic field Bp1 is changed depending on a pulse sequence. The FID signal may be measured for a measurement time t_measure from the time when the predetermined FLL driving time t_FLL has passed after the prepolarization magnetic field Bp1 is turned off.

Referring to FIG. 3B, the time interval t_P2 of applying the prepolarization magnetic field is different from the time interval t_P1 of applying the prepolarization magnetic field in FIG. 3A (S124). Accordingly, the initial amplitude of the FID signal varies depending on the degree of the polarization of the measurement target.

Figure 4:
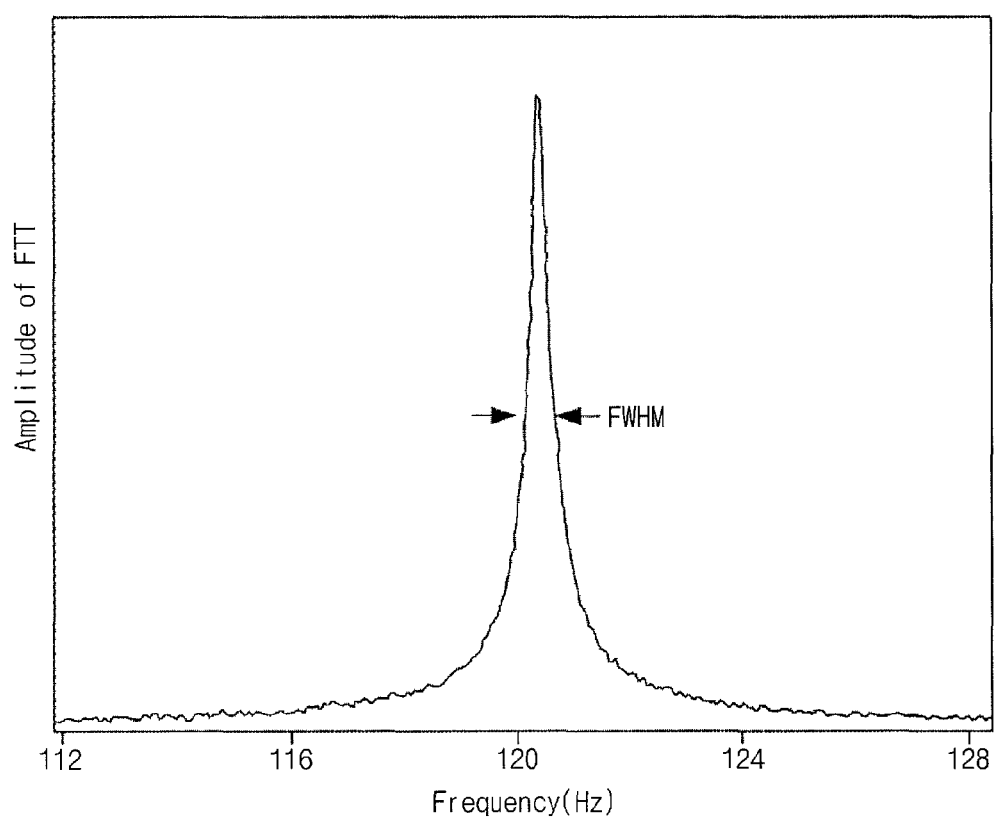
FIG. 4 shows a result of Fourier transformation of an FID signal obtained by the pulse sequence in FIG. 3A.

FIG. 4 is a result of Fourier transformation of an FID signal obtained by the pulse sequence in FIG. 3A.

FIG. 4 shows the amplitude at a resonance frequency of the hydrogen nucleus depending on the time interval of applying a prepolarization magnetic field.

Referring now to FIG. 4, there is shown the fast Fourier transformation (FFT) of a free induction decay (FID) signal of $^1$H proton of a measurement target. As shown in FIG. 4, the $T_2$* was about 2.5 seconds or more and a signal-to-noise ratio (SNR) was about 14.5. The FFT is performed after the zero-filling. A frequency peak appears about 120 Hz. A location of the frequency peak matches well with 120 Hz that is a resonance frequency of water corresponding to an applied readout magnetic field having the strength of 2.82 microTeslas. The Full-width-half maximum (FWHM) of a spectral resolution, which means a spatial resolution of an NMR system, is about 0.5 Hz.

Figure 5:
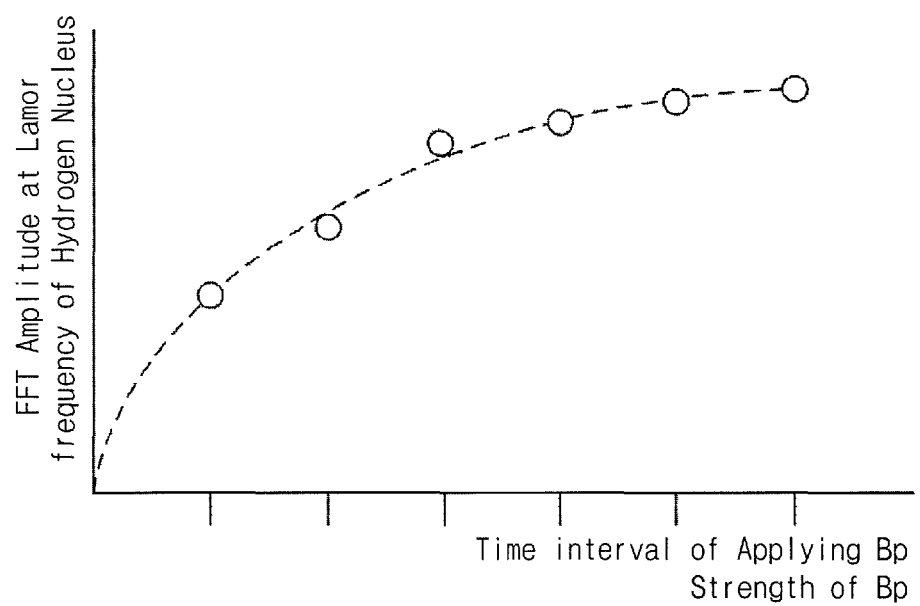
FIG. 5 shows an amplitude at Larmor frequency depending on the strength or time interval of the prepolarization magnetic field.

FIG. 5 shows an amplitude at Larmor frequency depending on the strength or time interval of the prepolarization magnetic field.

Referring to FIG. 5, the amplitude at a resonance frequency of the hydrogen nucleus varies depending on the time interval t_P or strength of a prepolarization magnetic field Bp1. The polarization of a measurement target is saturated as the strength or time interval of the prepolarization magnetic field increases. Accordingly, the polarization of the measurement target is dependent on the amplitude. As a result, the amplitude has the exponential functional dependency according to the time interval, and the $T_1$ may be obtained by fitting the exponential function (S142).

Figure 6:
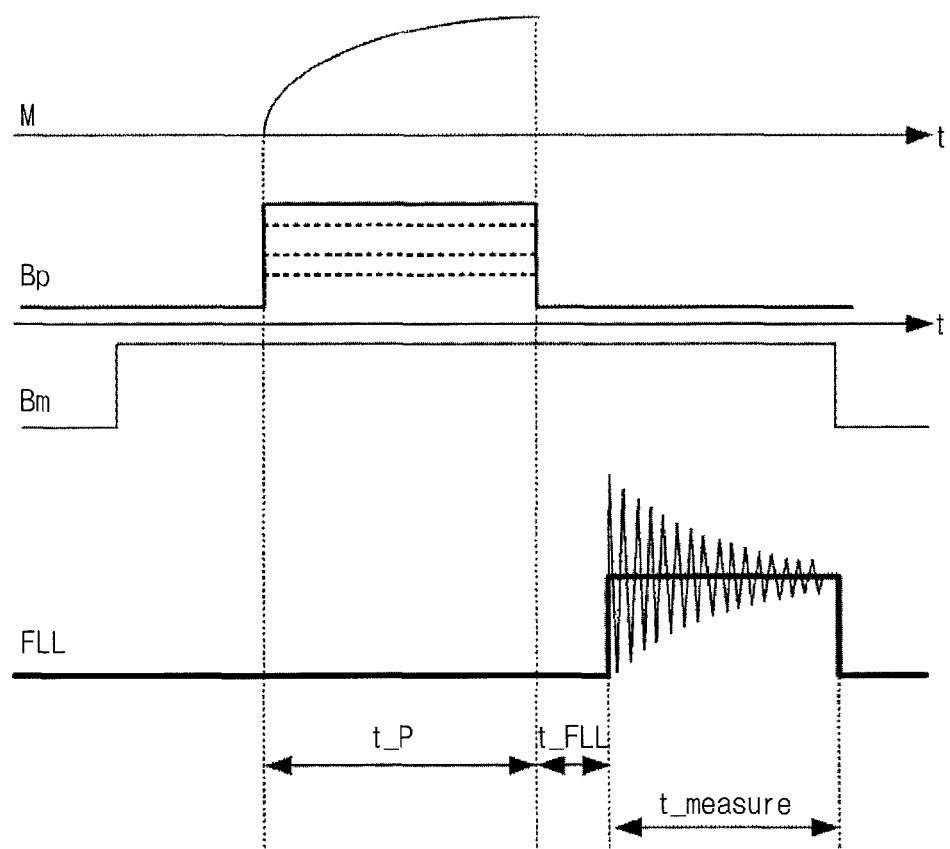
FIG. 6 illustrates a pulse sequence according to another embodiment of the present invention.

FIG. 6 illustrates a pulse sequence according to another embodiment of the present invention.

Referring to FIGS. 2 and 6, the $T_1$ may be obtained by measuring an FID signal while changing the strength of a prepolarization magnetic field Bp at fixed time interval of applying the prepolarization magnetic field Bp (S134). Accordingly, the degree of the polarization of the measurement target is decided depending on the strength of the prepolarization magnetic field Bp. The measured FID signal may be Fourier-transformed (S116). Thereafter, the Fourier-transformed amplitude according to a frequency is obtained (S118).

The amplitude at a resonance frequency of the hydrogen nucleus may be measured depending on the strength of a prepolarization magnetic field. The amplitude at the resonance frequency of the hydrogen nucleus depending on the strength of the prepolarization magnetic field is saturated as the strength increases. The amplitude may have the exponential functional dependency according to the strength, and the $T_1$ may be obtained by fitting the exponential function (S142).

The time interval t_P of a prepolarization magnetic field Bp is constant, and the strength of the prepolarization magnetic field Bp increases or decreases depending on a pulse sequence. An FID signal may be measured for a measurement time t_measure from the time when the predetermined FLL driving time t_FLL has passed after the prepolarization magnetic field Bp is turned off. Thus, the amplitude may be extracted at a resonance frequency of the hydrogen nucleus according to the strength of a prepolarization magnetic field at fixed time interval of the prepolarization magnetic field. The amplitude may have the exponential functional dependency according to the strength of the prepolarization magnetic field, and the $T_1$ may be extracted by the exponential functional dependency.

With respect to other nuclei such as the carbon and nitrogen other than the hydrogen, the $T_1$ and/or $T_2$ may be classified depending on the variety of a measurement target.

Figure 7:
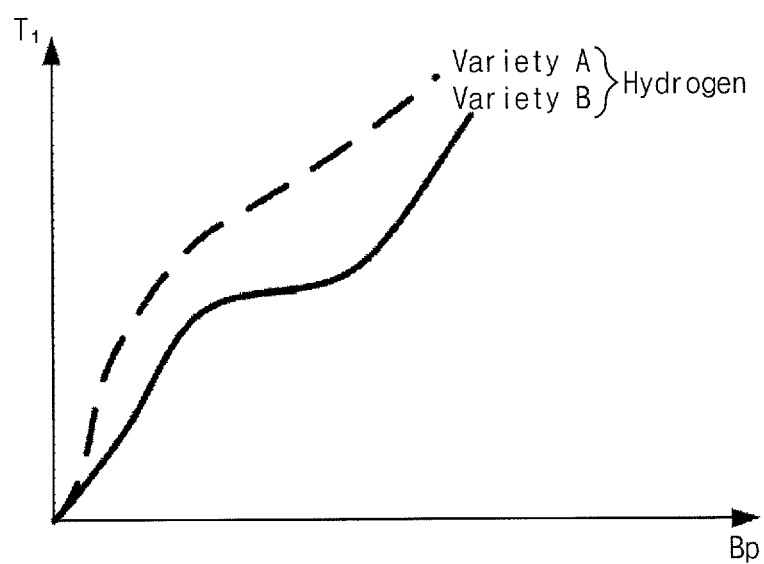
FIG. 7 illustrates a dependency of the $T_1$ depending on Bp according to an embodiment of the present invention.

FIG. 7 illustrates a dependency of $T_1$ depending on Bp according to an embodiment of the present invention.

Referring to FIG. 7, a variety "A" and a variety "B" may have different $T_1$ dependencies of the hydrogen nucleus according to a prepolarization magnetic field Bp. In addition, the variety "A" and the variety "B" may have dependencies of different tendencies of the carbon nucleus. In addition, the variety "A" and the variety "B" may have dependencies of different tendencies of the nitrogen nucleus. Thus, varieties may be discriminated with the $T_1$ dependencies according to the prepolarization magnetic field Bp.

Figure 8:
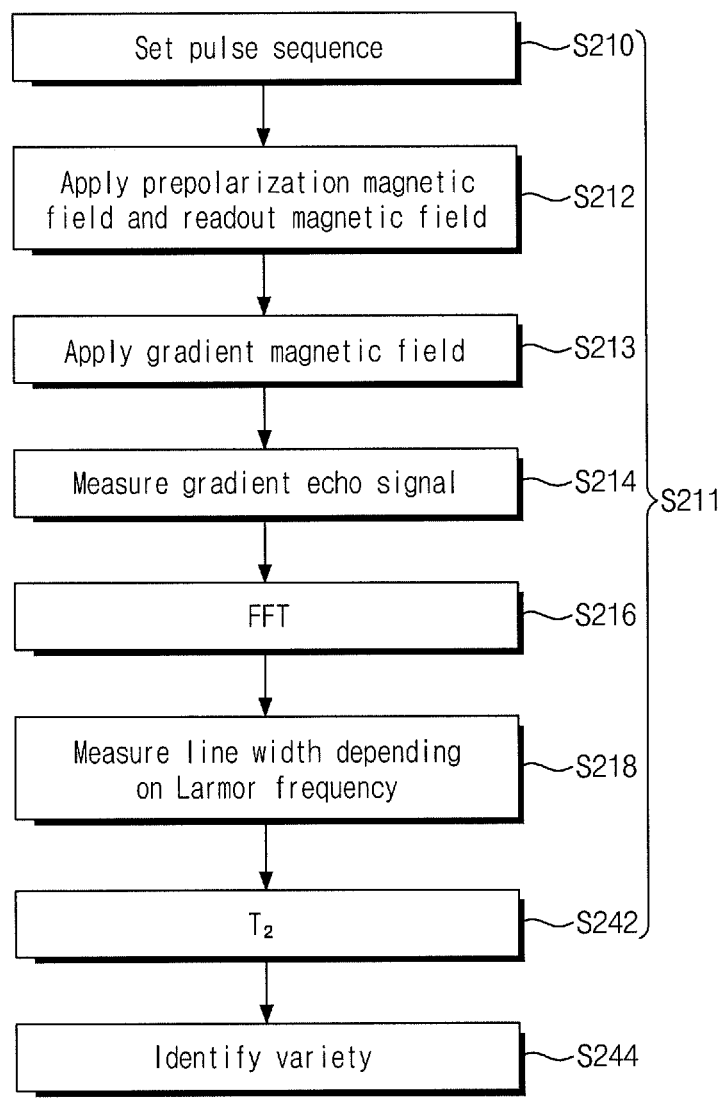
FIG. 8 illustrates a pulse sequence to measure the $T_2$ according to another embodiment of the present invention.

FIG. 8 illustrates a pulse sequence to measure the $T_2$ according to another embodiment of the present invention.

Figure 9:
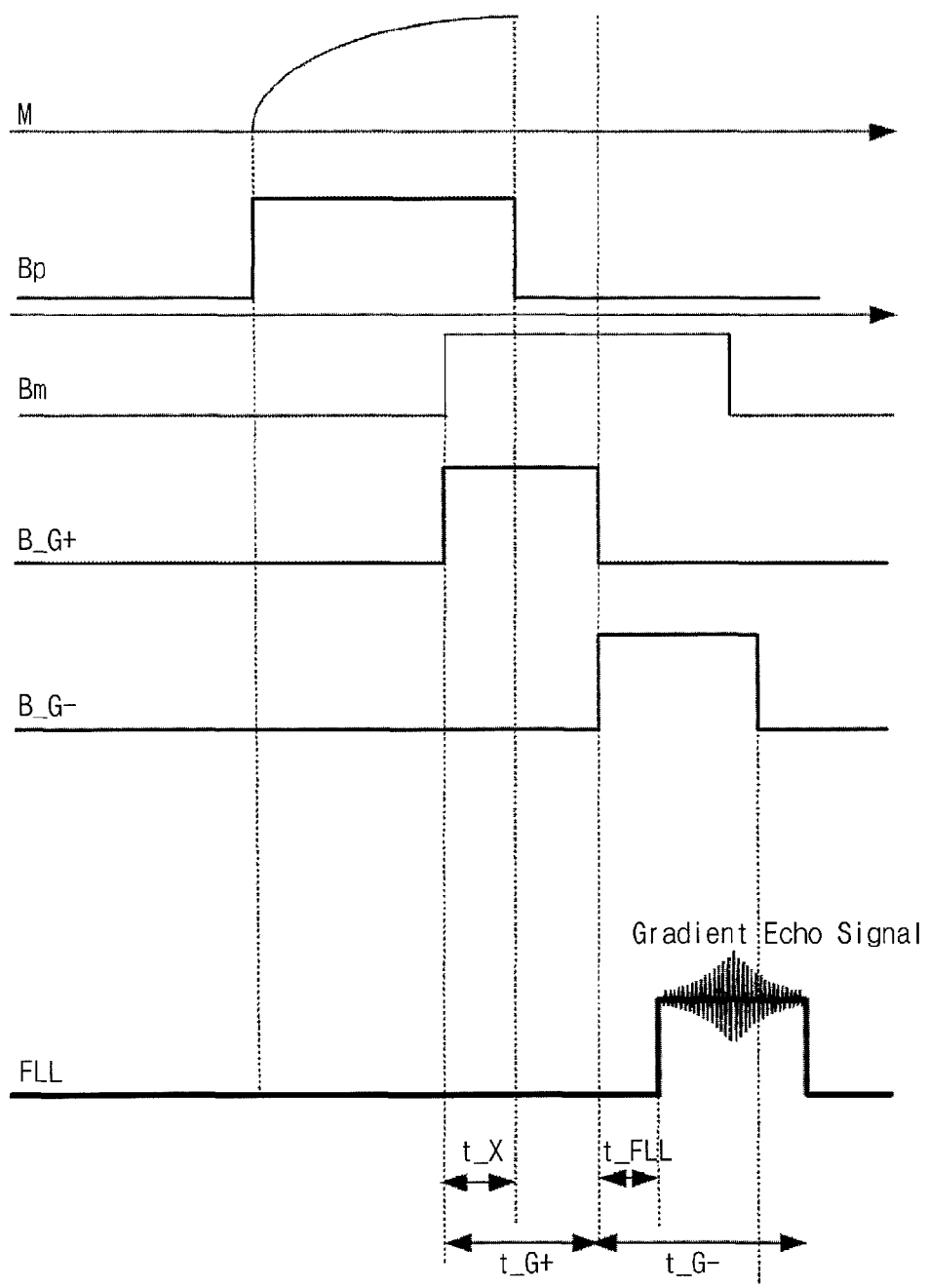
FIG. 9 illustrates a pulse sequence to measure the $T_2$ in FIG. 8.

FIG. 9 illustrates a pulse sequence to measure the $T_2$ in FIG. 8.

Referring to FIGS. 8 and 9, a prepolarization magnetic field Bp is applied, and a positive gradient magnetic field B_G+ is applied to a measurement target simultaneously to the time interval of applying the readout magnetic field Bm before the prepolarization magnetic field Bp is turned off. In addition, a negative gradient magnetic field B_G− is applied to the measurement target simultaneously when the positive gradient magnetic field B_G+ is turned off. Thus, the spins under dephasing at the measurement target are refocused by the negative gradient magnetic field B_G− with the opposite polarity. The refocusing may generate a gradient echo signal. The time interval of applying the positive gradient magnetic field B_G+ is t_G+, and the time interval of applying the negative gradient magnetic field B_G− is t_G−.

A pulse sequence was designed to turn on the readout magnetic field Bm and the positive gradient magnetic field B_G+ before the prepolarization magnetic field Bp is turned off. The time t_x of simultaneously turning on the positive gradient magnetic field B_G+ and the prepolarization magnetic field Bp is 30 milliseconds (ms). A pulse sequence was designed to turn on the negative gradient magnetic field B_G− simultaneously when the positive magnetic field B_G+ is turned off. It took a delay time of about 35 ms to reach a maximum voltage after the negative gradient magnetic field B_G− is turned on. After the negative gradient magnetic field B_G− is turned on, the time t_FLL for an FLL to start measurement is 8 ms.

The gradient echo signal may be Fourier-transformed. A reciprocal of the peak line width of the resonance frequency of the hydrogen nucleus indicates the T2.

An object discrimination method using an ultra-low magnetic field NMR may include measuring the spin-spin relaxation time $T_2$ of the measurement target using a gradient echo signal (S211) and classifying the measurement target using the spin-spin relaxation time $T_2$ (S244).

The operation S211 may include setting a pulse sequence suitable for individual relaxation time characteristics of the measurement target (S210), applying the prepolarization magnetic field and a readout magnetic field (S212), successively applying a positive gradient magnetic field and a negative gradient magnetic field (S213), measuring a gradient echo signal (S214), measuring the signal line width of the resonance frequency of a nucleus (S218) by Fourier-transform of the gradient echo signal (S216), and constructing the second parameter vector with the line width or a reciprocal of the line width depending on the resonance frequency of a nucleus (S242). A variety may be identified using the second parameter vector (S244).

Figure 10:
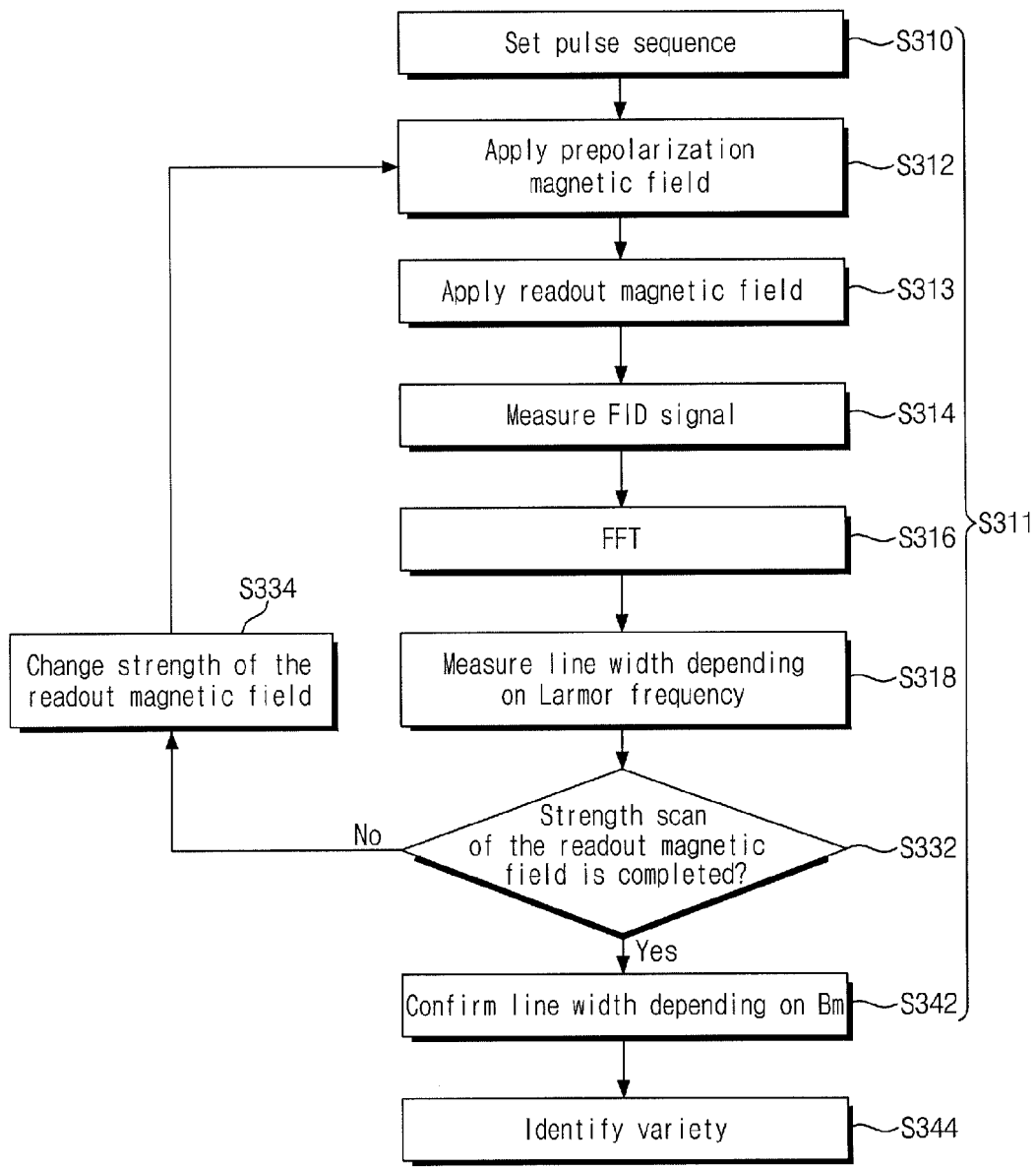
FIG. 10 illustrates an object discrimination method according to an embodiment of the present invention.

FIG. 10 illustrates an object discrimination method according to an embodiment of the present invention.

Figure 11:
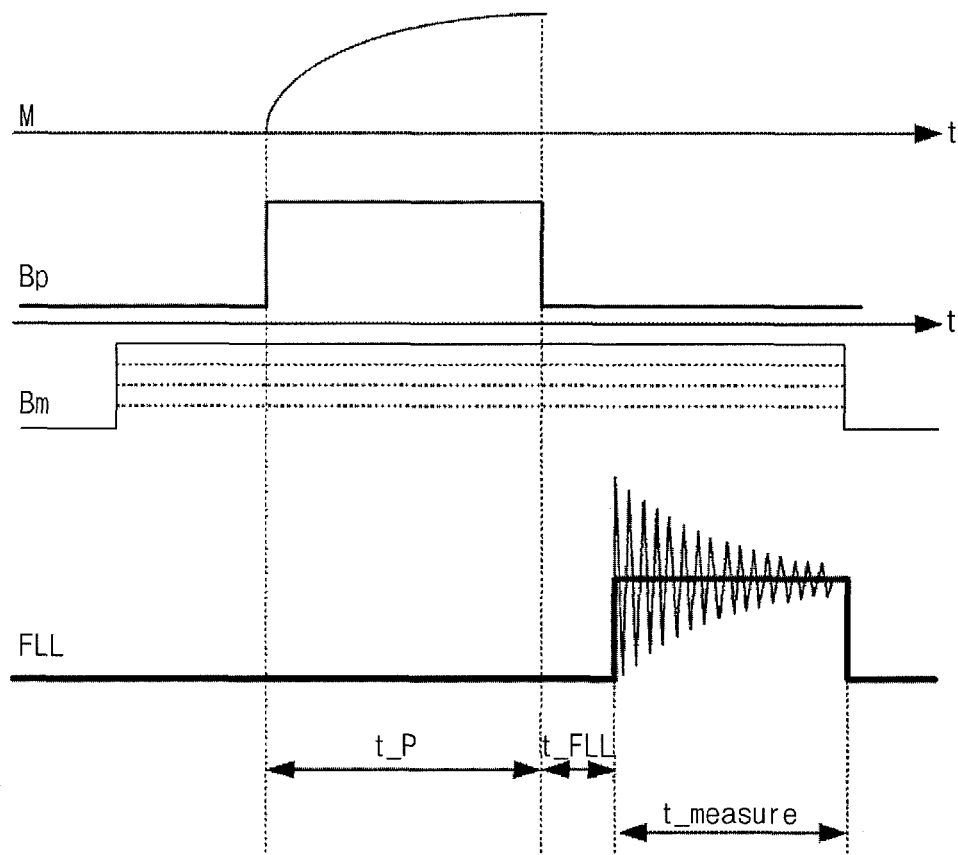
FIG. 11 illustrates a pulse sequence to measure the line width of a signal obtained by Fourier-transform of an FID signal in FIG. 10.

FIG. 11 illustrates a pulse sequence to measure the line width of a signal obtained by Fourier-transform of an FID signal in FIG. 10.

Figure 12:
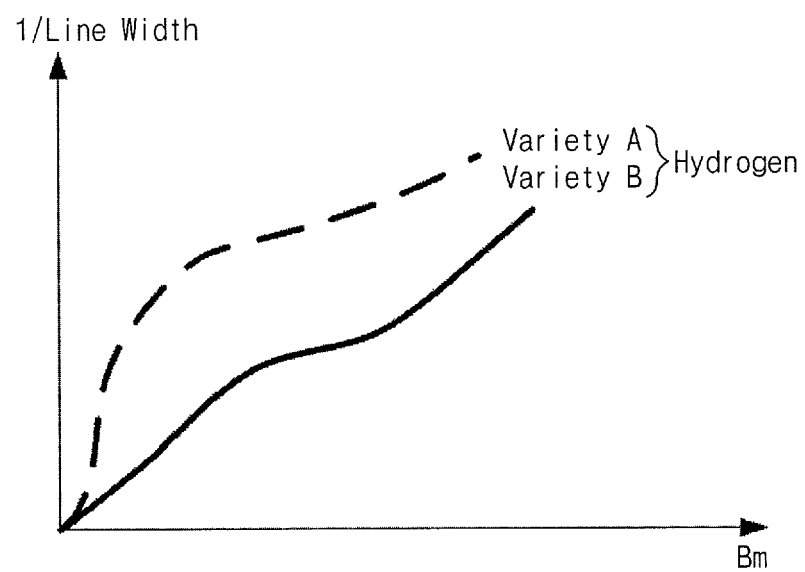
FIG. 12 shows virtual data obtained using the object discrimination method in FIG. 10.

FIG. 12 shows virtual data obtained using the object discrimination method in FIG. 10.

Referring to FIGS. 10 to 12, an object discrimination method using an ultra-low magnetic field NMR includes measuring the signal line width of the resonance frequency of a nucleus by Fourier-transforming the measured free induction decay (FID) signal while changing the strength of a readout magnetic field to a measurement target (S311) and classifying the measurement target using the signal line width of the resonance frequency of a nucleus (S344).

The operation S311 includes setting a pulse sequence suitable for individual relaxation time characteristics of the measurement target (S310), applying a prepolarization magnetic field (S312), applying the readout magnetic field (S313), measuring the FID signal (S314), measuring the signal line width of the resonance frequency of a nucleus by Fourier-transform of the FID signal (S316 and S318), changing the strength of the readout magnetic field (S334), and constructing the third parameter vector with the signal line width of the resonance frequency of a nucleus depending on the strength of the readout magnetic field by repeatedly measuring the above operations (S342). The variety of the measurement target is identified using the third parameter vector (S344).

A pulse sequence to measure line width of the resonance frequency of the hydrogen nucleus may apply a prepolarization magnetic field Bp1 and a readout magnetic field Bm sequentially or simultaneously. The readout magnetic field Bm is preferably applied before the prepolarization magnetic field Bp1 is turned off. The strength of the prepolarization magnetic field Bp1 is constant. The time interval t_P of applying the prepolarization magnetic field Bp1 is constant. The FID signal may be measured for a measurement time t_measure from the time when the predetermined FLL driving time t_FLL has passed after the prepolarization magnetic field Bp1 is turned off. The strength of the readout magnetic field Bm may be changed to increase or decrease depending on a pulse sequence. Thus, the line width of the resonance frequency of a nucleus depending on the strength of the readout magnetic field Bm may be used for the variety discrimination.

Figure 13:
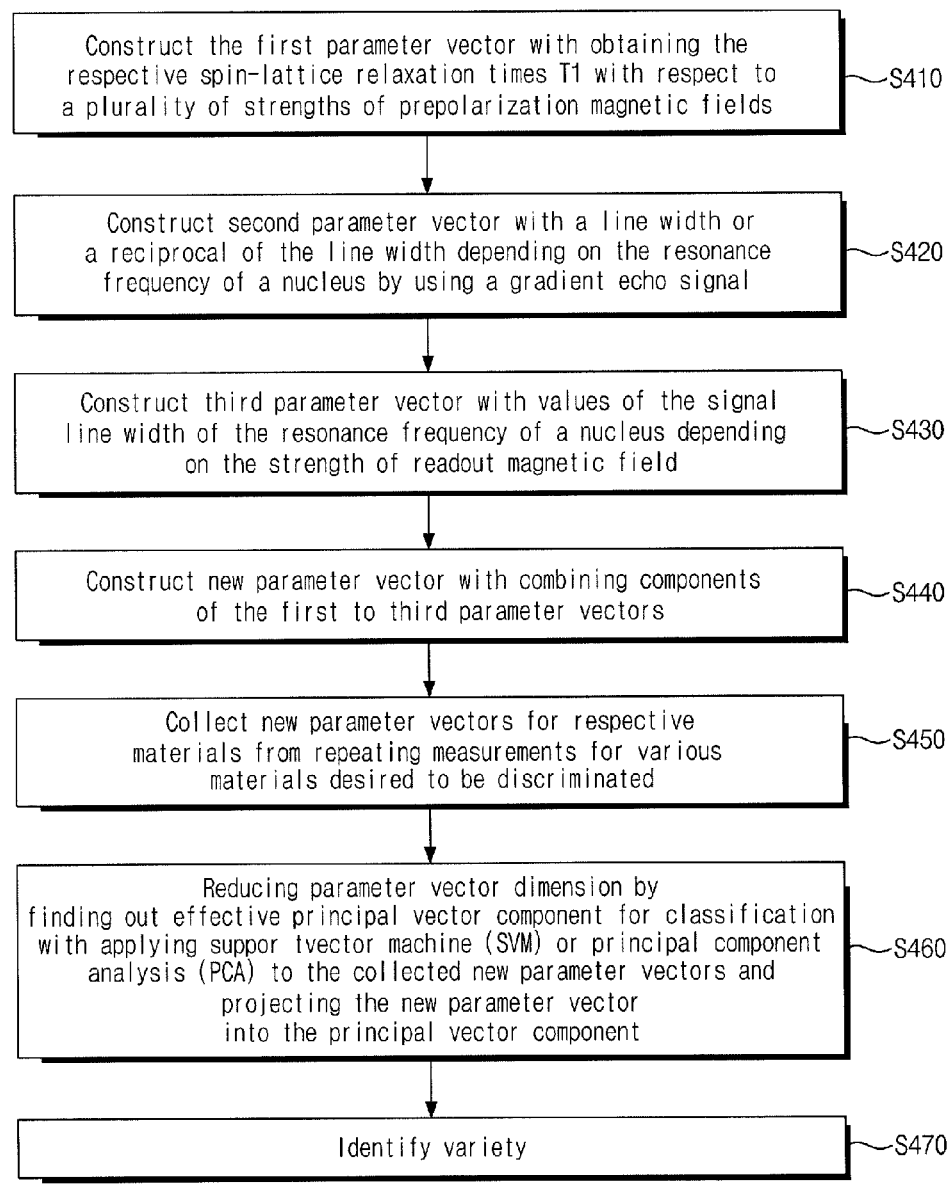
FIG. 13 is a flowchart illustrating an object discrimination method using an ultra-low magnetic field NMR according to another embodiment of the present invention.

FIG. 13 is a flowchart illustrating an object discrimination method using an ultra-low magnetic field NMR according to another embodiment of the present invention.

Referring to FIG. 13, the object discrimination method using an ultra-low magnetic field NMR includes constructing the first parameter vector with obtaining the respective spin-lattice relaxation times $T_1$ with respect to a plurality of strengths of prepolarization magnetic fields (S410), constructing the second parameter vector with a line width or a reciprocal $T_2$ of the line width depending on the resonance frequency of a nucleus by using a gradient echo signal (S420), constructing the third parameter vector with values of the signal line width of the resonance frequency of a nucleus depending on the strength of a readout magnetic field (S430), constructing a new parameter vector with combining components of the first to third parameter vectors (S440), and identifying the variety of a measurement target using the new parameter vector (S470).

An object discrimination method using an ultra-low magnetic field NMR according to a modified embodiment of the present invention includes constructing the first parameter vector with obtaining the respective spin-lattice relaxation times $T_1$ with respect to a plurality of strengths of prepolarization magnetic fields (S410), constructing the second parameter vector with a line width or a reciprocal $T_2$ of the line width depending on the resonance frequency of a nucleus by using a gradient echo signal (S420), constructing the third parameter vector with values of the signal line width of the resonance frequency of a nucleus depending on the strength of a readout magnetic field (S430), constructing a new parameter vector with combining components of the first to third parameter vectors (S440), collecting new parameter vectors for the respective materials from repeating measurements for various materials desired to be discriminated (S450), reducing a parameter vector dimension by finding out an effective principal vector component for classification with applying support vector machine (SVM) or principal component analysis (PCA) to the collected new parameter vectors and projecting the new parameter vector into the principal vector component (S460), and identifying the variety of the material using the component of the reduced parameter vector dimension (S470).

A parameter vector (g) may be constructed by combining a plurality of T1s obtained by a plurality of strengths of prepolarization magnetic fields, a plurality of signal line widths (or their reciprocals) obtained by a plurality of strengths of readout magnetic fields, and the $T_2$ obtained by a gradient echo signal as their respective dimensional values. For example, the parameter vector (g) may be given as follows: g=(T1@10 mT, T1@20 mT, T1@30 mT, . . . , T2).

The parameter vector constructed by repeatedly measuring a material group desired to be discriminated may be plotted on a multi-dimensional parameter vector space. Thus, a cluster on a parameter vector space depending on the material group may be observed. The discrimination of the material group on a parameter vector space may be mathematically done using the classification criteria through a method such as artificial neural network (ANN) or support vector machine (SVM) that is well known in a pattern recognition community.

If the number of parameters increases, it may take a bit of time to measure the parameters and discriminate the parameters in a parameter space. For this reason, a dimension of the parameter space may be reduced by applying the principal dimension where projecting the remaining dimensions to the principle dimension through SVM or principal component analysis.

The materials may be discriminated with higher speed using the reduced parameter vector component.

According to the above-described object discrimination method, varieties of agricultural and livestock products can be non-destructively discriminated without a conventional DNA test.

Although the present invention has been described in connection with the embodiment of the present invention illustrated in the accompanying drawings, it is not limited thereto. It will be apparent to those skilled in the art that various substitutions, modifications and changes may be made without departing from the scope and spirit of the present invention.

What is claimed is:

1. An object discrimination method using an ultra-low magnetic field nuclear magnetic resonance (NMR), the method comprising:
    measuring a signal line width of a resonance frequency of a nucleus by Fourier-transforming a measured free induction decay (FID) signal while changing the strength of a readout magnetic field to a measurement target; and
    classifying the measurement target using the signal line width of the resonance frequency of a nucleus.

2. The method as set forth in claim 1, wherein measuring the signal line width comprises:
    setting a pulse sequence suitable for individual relaxation time characteristics of the measurement target;
    applying a prepolarization magnetic field;
    applying the readout magnetic field;
    measuring a free induction decay (FID) signal;
    measuring the signal line width of the resonance frequency of a nucleus by Fourier-transform of the FID signal;
    changing the strength of the readout magnetic field; and
    constructing a third parameter vector with the signal line width of the resonance frequency of a nucleus depending on the strength of the readout magnetic field by repeatedly measuring the above operations,
    wherein the variety of the measurement target is identified using the third parameter vector.

3. An object discrimination method using an ultra-low magnetic field nuclear magnetic resonance (NMR), the method comprising:
    measuring respective spin-lattice relaxation times $T_1$ at a plurality of strengths of prepolarization magnetic fields with respect to a measurement target; and
    classifying the measurement target using the spin-lattice relaxation times,
    wherein measuring the respective spin-lattice relaxation times comprises:
    setting a pulse sequence suitable for individual relaxation time characteristics of the measurement target;
    applying a prepolarization magnetic field and a readout magnetic field;
    measuring a free induction decay (FID) signal;
    measuring a signal intensity or line width of a resonance frequency of a nucleus by Fourier-transform of the FID signal;
    changing a time interval of applying the prepolarization magnetic field;
    obtaining the spin-lattice relaxation time by fitting the signal intensity variation depending on the time interval of applying the prepolarization magnetic field; and
    constructing a first parameter vector with the respective spin-lattice relaxation times by repeatedly performing the above operations on a plurality of changed strengths of prepolarization magnetic fields,
    wherein the variety of the measurement target is identified using the first parameter vector.

4. The method as set forth in claim 3, further comprising:
    measuring a spin-spin relaxation time $T_2$ of the measurement target using a gradient echo signal; and
    classifying the measurement target using the spin-spin relaxation time.

5. An object discrimination method using an ultra-low magnetic field nuclear magnetic resonance (NMR), the method comprising:
    measuring respective spin-lattice relaxation times $T_1$ at a plurality of strengths of prepolarization magnetic fields with respect to a measurement target;
    classifying the measurement target using the spin-lattice relaxation times;
    measuring a spin-spin relaxation time $T_2$ of the measurement target using a gradient echo signal; and
    classifying the measurement target using the spin-spin relaxation time,
    wherein measuring the spin-spin relaxation time of the measurement target comprises:
    setting a pulse sequence suitable for individual relaxation time characteristics of the measurement target;
    applying a prepolarization magnetic field and a readout magnetic field;
    successively applying a positive gradient magnetic field and a negative gradient magnetic field;
    measuring a gradient echo signal;
    measuring a signal intensity or line width of a resonance frequency of a nucleus by Fourier-transform of the gradient echo signal; and
    constructing a second parameter vector with a line width or a reciprocal of the line width depending on the resonance frequency of a nucleus,
    wherein the variety of the measurement target is identified using the second parameter vector.

* * * * *